US012679852B2

(12) United States Patent
Koradin et al.

(10) Patent No.: US 12,679,852 B2
(45) Date of Patent: Jul. 14, 2026

(54) METHOD FOR PREPARING AN ENANTIOMERICALLY ENRICHED FORM OF 3-(2-CHLOROTHIAZOL-5-YL)-8-METHYL-7-OXO-6-PHENYL-2,3-DIHYDROTHIAZOLO [3,2-A]PYRIMIDIN-4-IUM-5-OLATE

(71) Applicant: BASF SE, Ludwigshafen (DE)

(72) Inventors: Christopher Koradin, Ludwigshafen (DE); Martin John McLaughlin, Liestal (CH); Roland Goetz, Ludwigshafen (DE); Rahul Kaduskar, Navi (IN); Harish Shinde, Navi (IN)

(73) Assignee: BASF SE, Ludwigshafen (DE)

( * ) Notice: Subject to any disclaimer, the term of this patent is extended or adjusted under 35 U.S.C. 154(b) by 374 days.

(21) Appl. No.: 18/272,820

(22) PCT Filed: Jan. 21, 2022

(86) PCT No.: PCT/EP2022/051368

§ 371 (c)(1),
(2) Date: Jul. 18, 2023

(87) PCT Pub. No.: WO2022/157323

PCT Pub. Date: Jul. 28, 2022

(65) Prior Publication Data

US 2024/0101575 A1 Mar. 28, 2024

(30) Foreign Application Priority Data

Jan. 22, 2021 (EP) .................................... 21153038

(51) Int. Cl.
*C07D 513/04* (2006.01)

(52) U.S. Cl.
CPC .................................. *C07D 513/04* (2013.01)

(58) Field of Classification Search
None
See application file for complete search history.

(56) References Cited

FOREIGN PATENT DOCUMENTS

| | | | |
|---|---|---|---|
| CN | 109970731 | B | 5/2020 |
| WO | WO-2014/167084 | A1 | 10/2014 |
| WO | WO-2018/177970 | A1 | 10/2018 |
| WO | WO-2018/197541 | A1 | 11/2018 |
| WO | WO-2018/202654 | A1 | 11/2018 |

OTHER PUBLICATIONS

European Patent Application No. 21153038.1, Extended European Search Report, dated May 7, 2021.
International Application No. PCT/EP2022/051368, International Search Report and Written Opinion, mailed Apr. 4, 2022.

*Primary Examiner* — Samantha L Shterengarts
(74) *Attorney, Agent, or Firm* — MARSHALL, GERSTEIN & BORUN LLP

(57) ABSTRACT

The present invention relates to a method for preparing an enantiomerically enriched form of 3-(2-chlorothiazol-5-yl)-8-methyl-7-oxo-6-phenyl-2,3-dihydrothiazolo[3,2-a]pyrimidin-4-ium-5-olate.

16 Claims, No Drawings

METHOD FOR PREPARING AN ENANTIOMERICALLY ENRICHED FORM OF 3-(2-CHLOROTHIAZOL-5-YL)-8-METHYL-7-OXO-6-PHENYL-2,3-DIHYDROTHIAZOLO [3,2-A]PYRIMIDIN-4-IUM-5-OLATE

CROSS-REFERENCE TO RELATED APPLICATIONS

This is the U.S. national phase of International Application No. PCT/EP2022/051368, filed Jan. 21, 2022, which claims the benefit of European Patent Application No. 21153038.1, filed Jan. 22, 2021.

The present invention relates to a method for preparing an enantiomerically enriched form of 3-(2-chlorothiazol-5-yl)-8-methyl-7-oxo-6-phenyl-2,3-dihydrothiazolo[3,2-a]pyrimidin-4-ium-5-olate.

TECHNICAL BACKGROUND 3-(2-Chlorothiazol-5-yl)-8-methyl-7-oxo-6-phenyl-2,3-dihydrothiazolo[3,2-a]pyrimidin-4-ium-5-olate and enantiomerically enriched forms thereof has insecticidal properties and is known, for example, from WO 2018/177970 or WO 2014/167084.

The methods thus far known for the preparation of this pyriminidium compound are cumbersome and not yet satisfactory.

In WO 2018/177970, WO 2018/197541 and WO 2018/202654, non-racemic 2,3-dihydrothiazolo[3,2-a]pyrimidinium compounds are prepared by reaction of a nonracemic 4-heteroaryl-substituted thiazolidin-2-imine with a 2-substituted malonic acid derivative. In WO 2018/177970 and WO 2018/197541, the non-racemic 4-heteroaryl-substituted thiazolidin-2-imine is in turn prepared by catalytic asymmetric hydrogenation of a 1-heteroaryl-substituted ethanimine carrying in 2-position a leaving group. The resulting amine is then reacted with an isothiocyanate to the thiazolidin-2-imine. The reaction sequence is described in WO 2018/197541 as follows:

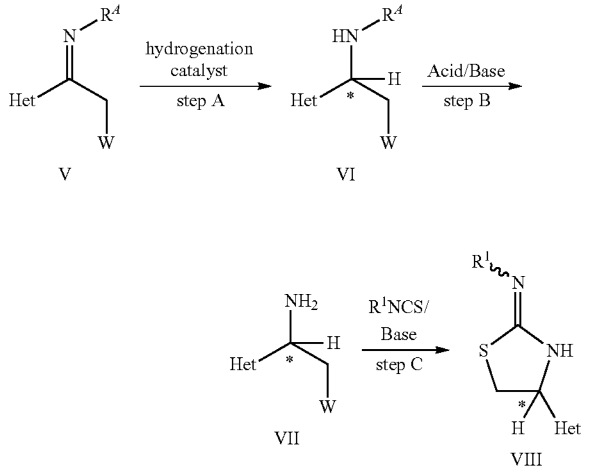

-continued

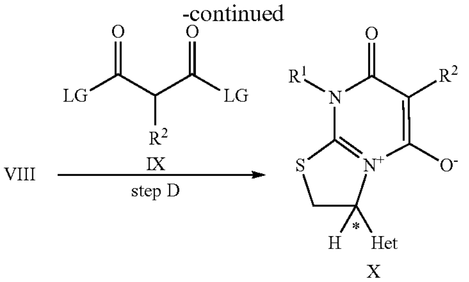

$R^A$ is a sulfanyl or sulfinyl, phosphoroxy, alkoxy or benzyl group; Het is optionally substituted pyridin-3-yl, thiazol-5-yl or pyrimidin-5-yl, W and LG are leaving groups, $R^1$ is a (cyclo)aliphatic group and $R^2$ is 5- or 6-membered carbo- or heterocyclic ring. In WO 2018/177970 the amine VII is obtained via another reaction path from the corresponding sulfinylimine.

WO 2018/177970 and WO 2018/202654 describe a further access to the non-racemic 4-heteroaryl-substituted thiazolidin-2-imine. This is here prepared starting from a heteroarylmethyl ketone, where the methyl group carries a leaving group, conversion of this leaving group into an alkylcarbonyloxy group, hydrolysis of the latter to a hydroxyl group, reaction of the resulting heteroarylhydroxymethyl ketone with a sulfamoyl halide to a 4-heteroaryl-5H-oxathiazole 2,2-dioxide, submission of the latter to a catalytic asymmetric hydrogenation to yield a non-racemic 4-heteroaryloxathiazolidine 2,2-dioxide and reaction thereof with an isothiocyanate to the thiazolidin-2-imine. The reaction sequence is described in WO 2018/202654 as follows:

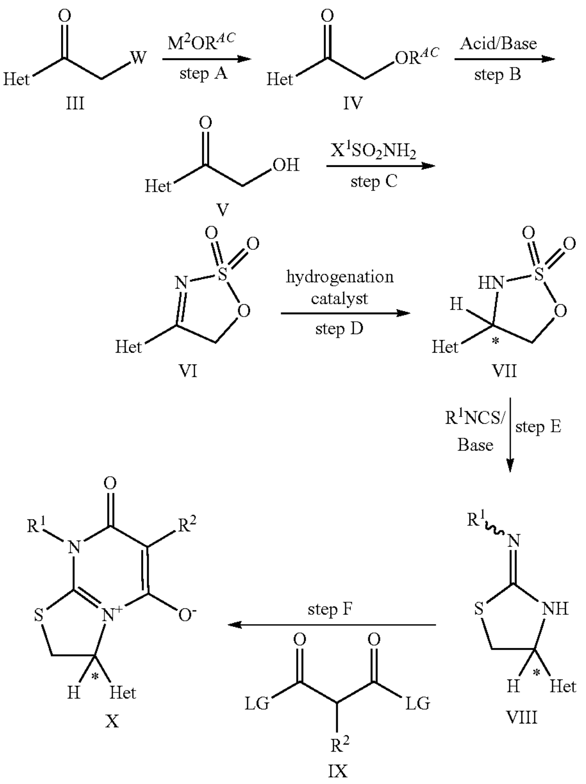

Het is optionally substituted pyridin-3-yl, thiazol-5-yl or pyrimidin-5-yl, W and LG are leaving groups, $M^2$ is Li, Na, K, Al, Ba, Cs, Ca or Mg, $R^{AC}$ is alkylcarbonyl, $X^1$ is halogen, $R^1$ is a (cyclo)aliphatic group and $R^2$ is 5- or 6-membered carbo- or heterocyclic ring.

These methods are however not very economic. Some reagents are expensive, recycling of some of the reagents which are not or not entirely consumed is difficult, the overall yield is not satisfactory and too many reaction steps are involved.

SUMMARY OF THE INVENTION

It was the object of the present invention to provide an economic process for the preparation of 3-(2-chlorothiazol-5-yl)-8-methyl-7-oxo-6-phenyl-2,3-dihydrothiazolo[3,2-a]pyrimidin-4-ium-5-olate and especially a process for the preparation of an enantiomerically enriched form thereof which yields the S or R enantiomer with high selectivity.

The problem is solved by a method for preparing an enantiomerically enriched form of 3-(2-chlorothiazol-5-yl)-8-methyl-7-oxo-6-phenyl-2,3-dihydrothiazolo[3,2-a]pyrimidin-4-ium-5-olate of the formula (I):

(I)

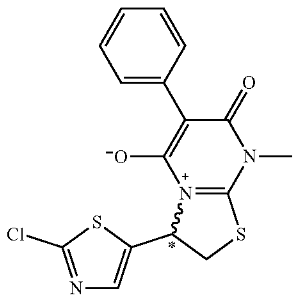

where the asterisk * shows the stereogenic center;

which method comprises reacting an enantiomerically enriched form of 2-[2-(2-chlorothiazol-5-yl)-2-hydroxy-ethyl]sulfanyl-6-hydroxy-3-methyl-5-phenyl-pyrimidin-4-one of the formula 1

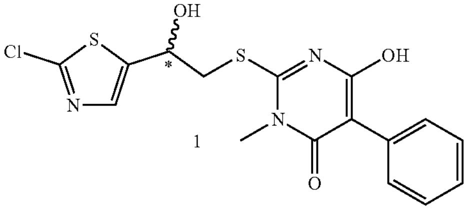 [SMILES: Cn1c(SCC(O)c2cnc(Cl)s2)nc(O)c(-c2ccccc2)c1=O]

1 where the asterisk * shows the stereogenic center;

or a tautomer or a mixture of different tautomers thereof, with an activating agent which enhances electrophilicity of the carbon atom marked with the asterisk in the compound of the formula 1 without promoting racemization at said carbon atom (or, alternatively expressed, promotes an intermolecular $S_N2$ attack at the carbon atom marked with the asterisk in the compound of the formula 1); to obtain an enantiomerically enriched form of the compound of the formula (I).

DETAILED DESCRIPTION OF THE INVENTION

Definitions

"Enantiomerically enriched form" of 3-(2-chlorothiazol-5-yl)-8-methyl-7-oxo-6-phenyl-2,3-dihydrothiazolo[3,2-a]pyrimidin-4-ium-5-olate of the formula (I) or the compound (I) in enantiomerically enriched form" and similar terms denote a non-racemic compound (1) in which either the S enantiomer or the R enantiomer predominates or is even present as only stereoisomer. The compound (I) has a single stereogenic center which is at the ring carbon atom carrying the thiazole ring and marked with an asterisk.

"Enantiomerically enriched form" of 2-[2-(2-chlorothiazol-5-yl)-2-hydroxy-ethyl]sulfanyl-6-hydroxy-3-methyl-5-phenyl-pyrimidin-4-one of the formula 1 or the compound 1 in enantiomerically enriched form" and similar terms denote a non-racemic compound 1 in which either the S enantiomer or the R enantiomer predominates or is even present as only stereoisomer. The compound 1 has a single stereogenic center which is at the aliphatic carbon atom carrying the OH group and marked with an asterisk.

The organic moieties mentioned below are—like the term halogen—collective terms for individual listings of the individual group members. The prefix $C_n$-$C_m$ indicates in each case the possible number of carbon atoms in the group.

The term "alkyl" as used herein and in the alkyl moieties of alkoxy refers to saturated straight-chain (linear) or branched hydrocarbon radicals having 1 to 3 ("$C_1$-$C_3$-alkyl"), 1 to 4 ("$C_1$-$C_4$-alkyl") or 1 to 6 ("$C_1$-$C_6$-alkyl") carbon atoms. $C_1$-$C_3$-Alkyl denotes a saturated linear or branched aliphatic radical with 1 to 3 carbon atoms. Examples are methyl, ethyl, n-propyl or isopropyl. $C_1$-$C_4$-Alkyl denotes a saturated linear or branched aliphatic radical with 1 to 4 carbon atoms. Examples are methyl, ethyl, n-propyl, isopropyl, n-butyl, sec-butyl, isobutyl and tert-butyl. $C_1$-$C_6$-Alkyl denotes a saturated linear or branched aliphatic radical with 1 to 4 carbon atoms. Examples are, in addition to those mentioned for $C_1$-$C_4$-alkyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "$C_3$-$C_6$-cycloalkyl" as used herein refers to monocyclic saturated hydrocarbon radicals having 3 to 6 carbon atoms as (only) ring members. Examples are cyclopropyl, cyclobutyl, cyclopentyl and cyclohexyl.

The term "$C_1$-$C_4$-alkoxy" refers to a $C_1$-$C_4$-alkyl group, as defined above, attached via an oxygen atom to the remainder of the molecule. Examples are methoxy, ethoxy, n-propoxy, 1-methylethoxy (isopropoxy), n-butoxy, 1-methylpropoxy (sec-butoxy), 2-methylpropoxy (isobutoxy) or 1,1-dimethylethoxy (tert-butoxy).

The term "$C_1$-$C_4$-alkoxy-$C_1$-$C_4$-alkyl" refers to a straight-chain or branched alkyl group having 1 to 4 carbon atoms, as defined above, where one hydrogen atom is replaced by a $C_1$-$C_4$-alkoxy group, as defined above. Examples are methoxymethyl, ethoxymethyl, propoxymethyl, isopropoxymethyl, n-butoxymethyl, sec-butoxymethyl, isobutoxymethyl, tert-butoxymethyl, 1-methoxyethyl, 1-ethoxyethyl, 1-propoxyethyl, 1-isopropoxyethyl, 1-n-butoxyethyl, 1-sec-butoxyethyl, 1-isobutoxyethyl, 1-tertbutoxyethyl, 2-methoxyethyl, 2-ethoxyethyl, 2-propoxyethyl, 2-isopropoxyethyl, 2-n-butoxyethyl, 2-sec-butoxyethyl, 2-isobutoxyethyl, 2-tert-butoxyethyl, 1-methoxypropyl, 1-ethoxypropyl, 1-propoxypropyl, 1-isopropoxypropyl, 1-n-butoxypropyl, 1-sec-butoxypropyl, 1-isobutoxypropyl, 1-tert-butoxypropyl, 2-methoxypropyl, 2-ethoxypropyl, 2-propoxypropyl, 2-isopropoxypropyl, 2-n-butoxypropyl, 2-sec-butoxypropyl, 2-isobutoxypropyl, 2-tert-butoxypropyl, 3-methoxypropyl, 3-ethoxypropyl, 3-propoxypropyl, 3-isopropoxypropyl, 3-n-butoxypropyl, 3-sec-butoxypropyl, 3-isobutoxypropyl, 3-tert-butoxypropyl and the like.

5- or 6-membered saturated heterocyclic rings containing one nitrogen atom as ring member and optionally one further heteroatom selected from N and O as ring member are for example pyrrolidine, pyrazolidine, imidazolidine, oxazolidine, isoxazolidine, piperidine, piperazine, or morpholine.

The compound 1 can be used as a tautomer thereof or as a mixture of different tautomeric forms. An example for a tautomeric form of the compound of the formula 1 as depicted above is the following formula:

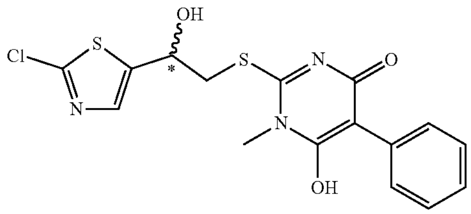 [SMILES: Cn1c(SCC(O)c2cnc(Cl)s2)nc(=O)c(-c2ccccc2)c1O]

Mixtures of different tautomeric forms are for example mixtures of this tautomer the tautomer depicted above as formula 1.

For the sake of simplicity, in the following only compound 1 is mentioned. Nevertheless, all embodiments also relate to its tautomers and mixtures of different tautomeric forms thereof.

The condensed zwitterionic ring of the compound of formula (I) is mesomerically stabilized. The mesomeric forms of the condensed ring can for example be expressed in different isoelectronic formulae with the positive and negative charges distributed on different atoms, such as shown in the following:

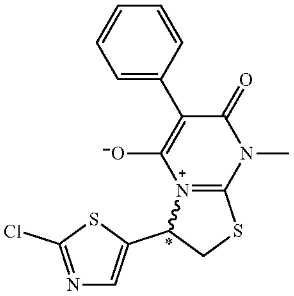

-continued

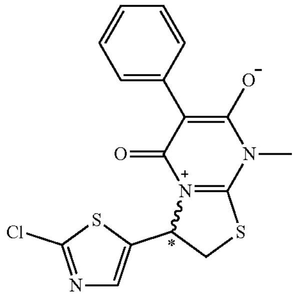

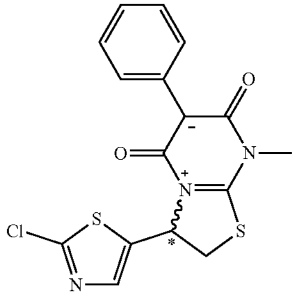

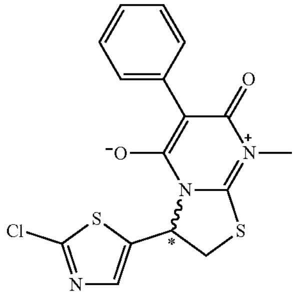

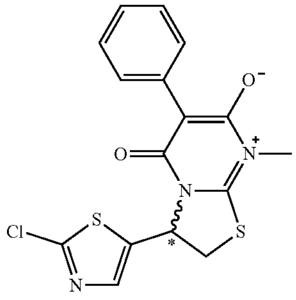

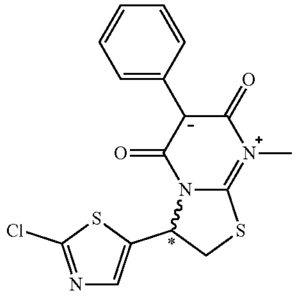

-continued

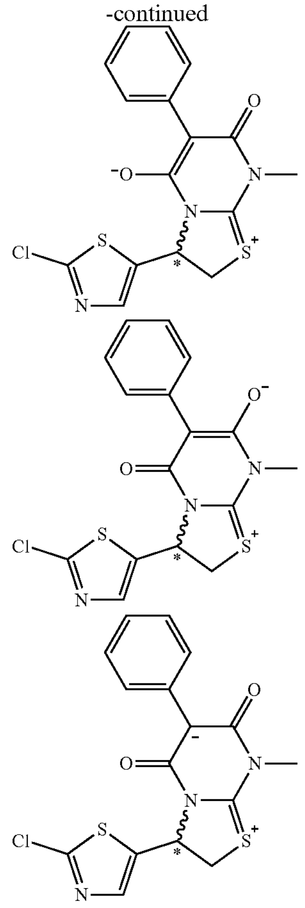

Embodiments (E.x) of the Invention

General and preferred embodiments E.x are summarized in the following, non-exhaustive list. Further preferred embodiments become apparent from the paragraphs following this list.

E.1. A method for preparing an enantiomerically enriched form of 3-(2-chlorothiazol-5-yl)-8-methyl-7-oxo-6-phenyl-2,3-dihydrothiazolo[3,2-a]pyrimidin-4-ium-5-olate of the formula (I):

(I)

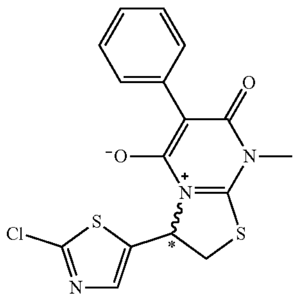

where the asterisk * shows the stereogenic center;

which method comprises reacting an enantiomerically enriched form of 2-[2-(2-chlorothiazol-5-yl)-2-hydroxy-ethyl]sulfanyl-6-hydroxy-3-methyl-5-phenylpyrimidin-4-one of the formula 1

1

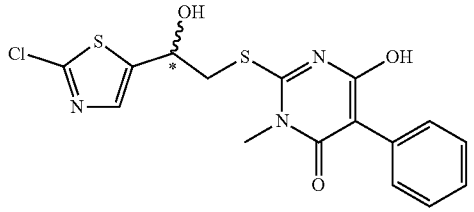

where the asterisk * shows the stereogenic center;

with an activating agent which enhances electrophilicity of the carbon atom marked with the asterisk in the compound of the formula 1 without promoting racemization at said carbon atom (alternatively expressed: promotes an intermolecular $S_N2$ attack at the carbon atom marked with the asterisk in the compound of the formula 1);

to obtain an enantiomerically enriched form of the compound of the formula (I).

E.2. The method according to embodiment E.1, where the activating agent is selected from the group consisting of $P(OR^1)_2Cl$, $P(OR^1)Cl_2$, $P(=O)(OR^1)_2Cl$, $P(=O)(OR^1)Cl_2$, where each $R^1$ in the four aforementioned compounds is independently $C_1$-$C_4$-alkyl; $PCl_3$, $P(=O)Cl_3$, polyphosphoric acid, $P_4O_{10}$, Mitsunobu-type reagents, triphenylphosphine in combination with a halogenating agent, $SO_3$ complexes with Lewis bases selected from amines, carboxamides and heteroaromatic compounds containing 1, 2 or 3 basic nitrogen ring atoms; $S(O)Cl_2$, $CH_3S(O)_2Cl$, carbonyldiimidazole (CDI), Vilsmeier reagent, complexes of N,N-dimethylformamide and/or N,N-dimethylacetamide with a Lewis acid; and mixtures of two or more of the aforementioned activating agents.

E.3. The method according to embodiment E.2, where the activating agent is selected from the group consisting of $P(OR^1)_2Cl$, $P(OR^1)Cl_2$, $P(=O)(OR^1)_2Cl$, where each $R^1$ in the three aforementioned compounds is independently $C_1$-$C_4$-alkyl; $PCl_3$, $P(O)Cl_3$, $SO_3$/dimethyl formamide complex, $SOC_2$, $CH_3S(=O)_2Cl$, CDI and Mitsunobu-type reagents.

E.4. The method according to embodiment E.3, where the activating agent is selected from the group consisting of dimethyl chlorophosphite ($P(OCH_3)_2Cl$), diethyl chlorophosphite ($P(OCH_2CH_3)_2Cl$), methyl dichlorophosphite ($P(OCH_3)Cl_2$), ethyl dichlorophosphite ($P(OCH_2CH_3)Cl_2$), $PCl_3$, $P(O)Cl_3$, $SOC_2$, $CH_3S(=O)_2Cl$, CDI and Mitsunobu-type reagents.

E.5. The method according to embodiment E.4, where the activating agent is selected from the group consisting of dimethyl chlorophosphite ($P(OCH_3)_2Cl$), diethyl chlorophosphite ($P(OCH_2CH_3)_2Cl$), methyl dichlorophosphite ($P(OCH_3)Cl_2$), ethyl dichlorophosphite ($P(OCH_2CH_3)Cl_2$), $PCl_3$ and $P(O)Cl_3$; in particular from dimethyl chlorophosphite ($P(OCH_3)_2Cl$), diethyl chlorophosphite ($P(OCH_2CH_3)_2$ Cl) and $PCl_3$.

E.6. The method according to embodiment E.3, where the activating agent is selected from the group consisting of $P(OR^1)_2Cl$, $P(OR^1)Cl_2$, $P(=O)(OR^1)_2Cl$, where each $R^1$ in the three aforementioned compounds is independently $C_1$-$C_4$-alkyl; $PCl_3$, $P(O)Cl_3$, $SO_3$/dimethyl formamide complex, $CH_3S(=O)_2Cl$ and CDI.

E.7. The method according to embodiment E.6, where the activating agent is selected from the group consisting of dimethyl chlorophosphite ($P(OCH_3)_2Cl$), diethyl chlorophosphite ($P(OCH_2CH_3)_2Cl$), methyl dichlorophosphite ($P(OCH_3)Cl_2$), ethyl dichlorophosphite ($P(OCH_2CH_3)Cl_2$), $PCl_3$, $P(O)Cl_3$, $SO_3$/dimethyl formamide complex and CDI; in particular from dimethyl chlorophosphite ($P(OCH_3)_2Cl$), diethyl chlorophosphite ($P(OCH_2CH_3)_2Cl$), methyl dichlorophosphite ($P(OCH_3)Cl_2$), ethyl dichlorophosphite ($P(OCH_2CH_3)Cl_2$), $PCl_3$ and $SO_3$/dimethyl formamide complex.

E.8. The method according to any of embodiments E.5 or E.7, where the activating agent is selected from the group consisting of dimethyl chlorophosphite ($P(OCH_3)_2Cl$) and diethyl chlorophosphite ($P(OCH_2CH_3)_2Cl$).

E.9. The method according to any of the preceding embodiments, where the compound of the formula 1 and the activating agent are used in a molar ratio of from 10:1 to 1:10.

E.10. The method according to embodiment E.9, where the compound of the formula 1 and the activating agent are used in a molar ratio of from 2:1 to 1:5.

E.11. The method according to embodiment E.10, where the compound of the formula 1 and the activating agent are used in a molar ratio of from 1:1 to 1:4.

E.12. The method according to embodiment E.11, where the compound of the formula 1 and the activating agent are used in a molar ratio of from 1:1 to 1:3.

E.13. The method according to embodiment E.12, where the compound of the formula 1 and the activating agent are used in a molar ratio of from 1:1 to 1:2.

E.14. The method according to any of the preceding embodiments, where the reaction is carried out at a temperature of from −80 to 120° C.

E.15. The method according to embodiment E.14, where the reaction is carried out at a temperature of from −20 to 100° C.

E.16. The method according to embodiment E.15, where the reaction is carried out at a temperature of from −10 to 90° C.

E.17. The method according to any of the preceding embodiments, where the reaction is carried out in the presence of a solvent.

E.18. The method according to embodiment E.17, where the solvent is selected from the group consisting of polar aprotic solvents, mixtures of polar aprotic solvents and water, $C_1$-$C_4$-alkyl acetates, chlorinated alkanes, aromatic solvents, heterocyclic solvents and mixtures thereof.

E.19. The method according to embodiment E.18, where the solvent is selected from the group consisting of dimethylformamide, diethylformamide, dibutylformamide, dimethylacetamide, tetrahydrofuran, mixtures of tetrahydrofuran and water, 2-methyltetrahydrofuran, the dioxanes, dimethylsulfoxide, acetonitrile, N-methylpyrrolidone, N-(n-butyl)-methylpyrrolidone, N-(tert-butyl)-methylpyrrolidone, sulfolane, dimethylcarbonate, diethylcarbonate, propylene carbonate, γ-valerolactone, N,N,N',N'-tetrabutyl urea, 1,3-dimethyl-2-imidazolinone, ethyl acetate, isopropyl acetate, dichloromethane, trichloromethane, dichloroethane, benzene, toluene, trifluorotoluene, the xylenes, chlorobenzene, dichlorobenzene, 4-formyl-morpholine, dihydrolevoglucosenone (Cyrene®) and mixtures thereof.

E.20. The method according to embodiment E.19, where the solvent is selected from the group consisting of dimethylformamide, diethylformamide, dibutylformamide, dimethylacetamide, tetrahydrofuran, mixtures of tetrahydrofuran and water, 2-methyltetrahydrofuran, 1,4-dioxane, acetonitrile, ethyl acetate, dichloromethane, toluene, chlorobenzene and mixtures thereof.

E.21. The method according to embodiment E.20, where the solvent is selected from the group consisting of dimethylformamide, dimethylacetamide, tetrahydrofuran, 2-methyltetrahydrofuran, acetonitrile, dichloromethane, toluene and mixtures thereof.

E.22. The method according to embodiment E.21, where the solvent is selected from the group consisting of tetrahydrofuran, 2-methyltetrahydrofuran, acetonitrile, dichloromethane, toluene and mixtures thereof.

E.23. The method according to any of the preceding embodiments, where the reaction is carried out in the presence of a base.

E.24. The method according to embodiment E.23, where the base is selected from the group consisting of alkali metal hydroxides, amines of the formula $NR^1R^2R^3$, where $R^1$, $R^2$ and $R^3$, independently of each other, are selected from the group consisting of hydrogen, $C_1$-$C_6$-alkyl, $C_3$-$C_6$-cycloalkyl, $C_1$-$C_4$-alkoxy and $C_1$-$C_4$-alkoxy-$C_1$-$C_4$-alkyl, where at least one of $R^1$, $R^2$ and $R^3$ is not hydrogen; diamines of the formula $NR^1R^2$-A-$NR^3R^4$, where $R^1$, $R^2$, $R^3$ and $R^4$, independently of each other, are selected from the group consisting of hydrogen, $C_1$-$C_6$-alkyl, $C_3$-$C_6$-cycloalkyl, $C_1$-$C_4$-alkoxy and $C_1$-$C_4$-alkoxy-$C_1$-$C_4$-alkyl, and A is $(CH_2)_2$ or $(CH_2)_3$; and a 5- or 6-membered saturated heterocyclic ring containing one nitrogen atom as ring member and optionally one further heteroatom selected from N and O as ring member, where the ring may carry 1 to 6 $C_1$-$C_4$-alkyl groups and/or 1 or 2 OH groups.

E.25. The method according to embodiment E.24, where the base is selected from the group consisting of LiOH, NaOH, KOH, diethylamine, triethylamine, tributylamine, diisopropylethylamine, dimethylisopropylamine, ethyl-tert-butylamine, isopropyl-tert-butylamine, (2-methoxyethyl)methylamine, N,N-dicyclohexylmethylamine, N-cyclohexyldimethylamine, N,N,N',N'-tetramethylethylenediamine, N,N,N',N'-tetramethylpropylene-1,3-diamine, piperdine, N-methylpiperidine, 2,2,6,6-tetramethylpiperidine, N-methyl-2,6,6-tetramethylpiperidine, N-methyl-4-hydroxy-2,2,6,6-tetramethylpiperidine, morpholine and N-methylmorpholine, where the bases can be used on supported from (i.e. on a support material).

E.26. The method according to embodiment E.25, where the base is selected from the group consisting of triethylamine, tributylamine and diisopropylethylamine.

E.27. The method according to any of embodiments E.1 to E.22, where the reaction is carried out in the absence of a base.

E.28. The method according to any of the preceding embodiments, for preparing (3R)-3-(2-chlorothiazol-5-yl)-8-methyl-7-oxo-6-phenyl-2,3-dihydrothiazolo[3,2-a]pyrimidin-4-ium-5-olate of the formula (I-R)

(I-R)

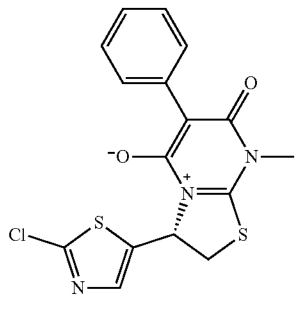

in an enantiomeric excess of at least 55% ee, which method comprises reacting 2-[(2S)-2-(2-chlorothiazol-5-yl)-2-hydroxyethyl]sulfanyl-6-hydroxy-3-methyl-5-phenyl-pyrimidin-4-one of the formula 1-S

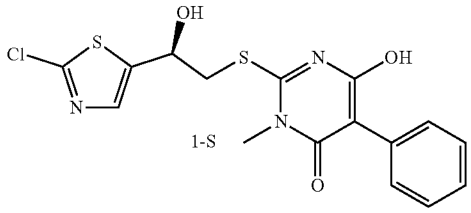 [SMILES: Cn1c(SC[C@H](O)c2cnc(Cl)s2)nc(O)c(-c2ccccc2)c1=O]

1-S with an activating agent as defined in any of embodiments E.1 to E.13.

E.29. The method according to embodiment E.28, for preparing (3R)-3-(2-chlorothiazol-5-yl)-8-methyl-7-oxo-6-phenyl-2,3-dihydrothiazolo[3,2-a]pyrimidin-4-ium-5-olate of the formula (I-R) in an enantiomeric excess of at least 60% ee.

E.30. The method according to embodiment E.29, for preparing (3R)-3-(2-chlorothiazol-5-yl)-8-methyl-7-oxo-6-phenyl-2,3-dihydrothiazolo[3,2-a]pyrimidin-4-ium-5-olate of the formula (I-R) in an enantiomeric excess of at least 70% ee.

E.31. The method according to embodiment E.30, for preparing (3R)-3-(2-chlorothiazol-5-yl)-8-methyl-7-oxo-6-phenyl-2,3-dihydrothiazolo[3,2-a]pyrimidin-4-ium-5-olate of the formula (I-R) in an enantiomeric excess of at least 80% ee.

E.32. The method according to embodiment E.31, for preparing (3R)-3-(2-chlorothiazol-5-yl)-8-methyl-7-oxo-6-phenyl-2,3-dihydrothiazolo[3,2-a]pyrimidin-4-ium-5-olate of the formula (I-R) in an enantiomeric excess of at least 90% ee.

E.33. The method according to any of embodiments E.1 to E.27, for preparing (3S)-3-(2-chlorothiazol-5-yl)-8-methyl-7-oxo-6-phenyl-2,3-dihydrothiazolo[3,2-a]pyrimidin-4-ium-5-olate of the formula (I-S)

(I-S)

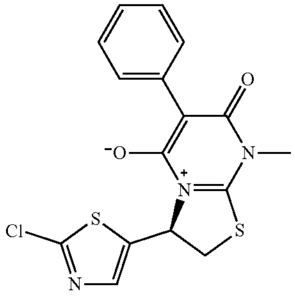

in an enantiomeric excess of at least 55% ee;

which method comprises reacting 2-[(2R)-2-(2-chlorothiazol-5-yl)-2-hydroxyethyl]sulfanyl-6-hydroxy-3-methyl-5-phenyl-pyrimidin-4-one of the formula 1-R

1-R

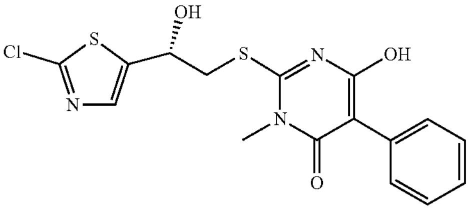

with an activating agent as defined in any of claims E.1 to E.13.

E.34. The method according to embodiment E.33, for preparing (3S)-3-(2-chlorothiazol-5-yl)-8-methyl-7-oxo-6-phenyl-2,3-dihydrothiazolo[3,2-a]pyrimidin-4-ium-5-olate of the formula (I-S) in an enantiomeric excess of at least 60% ee.

E.35. The method according to embodiment E.34, for preparing (3S)-3-(2-chlorothiazol-5-yl)-8-methyl-7-oxo-6-phenyl-2,3-dihydrothiazolo[3,2-a]pyrimidin-4-ium-5-olate of the formula (I-S) in an enantiomeric excess of at least 70% ee.

E.36. The method according to embodiment E.35, for preparing (3S)-3-(2-chlorothiazol-5-yl)-8-methyl-7-oxo-6-phenyl-2,3-dihydrothiazolo[3,2-a]pyrimidin-4-ium-5-olate of the formula (I-S) in an enantiomeric excess of at least 80% ee.

E.37. The method according to embodiment E.36, for preparing (3S)-3-(2-chlorothiazol-5-yl)-8-methyl-7-oxo-6-phenyl-2,3-dihydrothiazolo[3,2-a]pyrimidin-4-ium-5-olate of the formula (1-S) in an enantiomeric excess of at least 90% ee.

The reaction sequence can be depicted as follows:

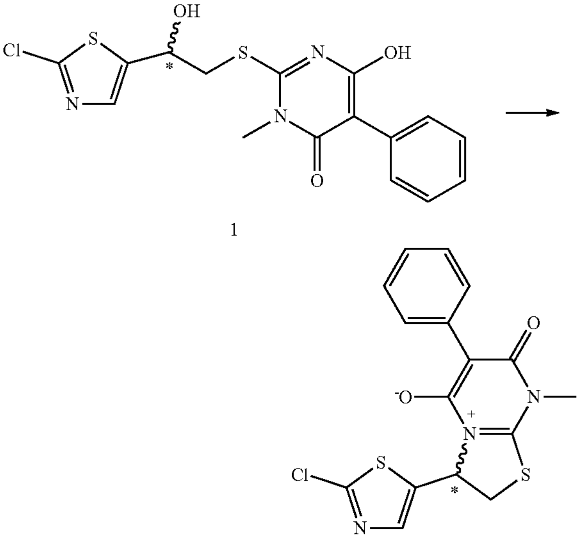

1

(I)

The activating agent is a compound which enhances electrophilicity of the carbon atom marked with the asterisk in the compound of the formula 1 without promoting racemization at said carbon atom. The reaction of 1 to the compound (I) is an intramolecular nucleophilic substitution in which the unsubstituted nitrogen atom of the pyrimidinone ring attacks the aliphatic carbon atom marked with the asterisk and substitutes the OH group, thus forming a condensed ring system. To preserve the chiral information of 1 in compound (I) to a maximum extent, conditions of this reaction are expediently such that racemization at the carbon atom marked with the asterisk is suppressed or at least minimized. This is expediently done by ensuring a nucleophilic attack under $S_N2$ conditions. The activating agent is thus alternatively defined as a compound which promotes an intermolecular $S_N2$ attack at the carbon atom marked with the asterisk in the compound of the formula 1.

Suitable activating agents are oxygenophilic compounds, such as various phosphorus compounds, but also certain compounds or compositions of compounds with Lewis acid properties.

Preferably, the activating agent is selected from the group consisting of $P(OR^1)_2Cl$, $P(OR^1)Cl_2$, $P(=O)(OR^1)_2Cl$, $P(=O)(OR^1)Cl_2$, where each $R^1$ in the four aforementioned compounds is independently $C_1$-$C_4$-alkyl; $PCl_3$, $P(=O)Cl_3$, polyphosphoric acid, $P_4O_{10}$, Mitsunobu-type reagents, triphenylphosphine in combination with a halogenating agent, $SO_3$ complexes with Lewis bases selected from amines, carboxamides and heteroaromatic compounds containing 1, 2 or 3 basic nitrogen ring atoms; $S(O)Cl_2$ (thionyl chloride), $CH_3S(O)_2Cl$ (mesyl chloride; methanesulfonyl chloride), carbonyldiimidazole (CDI), Vilsmeier reagent, complexes of N,N-dimethylformamide and/or N,N-dimethylacetamide with a Lewis acid; and mixtures of two or more of the aforementioned activating agents.

Mitsunobu-type reagents are combinations of triphenylphosphine with an azodicarboxylate, such as diethylazodicarboxylate (DEAD) or diisopropylazodicarboxylate (DIAD), or combinations of triphenylphosphine with an azodicarboxamide, such as tetramethylazodicarboxamide (TMAD). These combinations are either used as mixtures or are admixed in situ during reaction. Expediently, they can be used as commercially available mixtures.

Examples for halogenating agents to be used in combination with triphenylphosphine are N-chlorosuccinimide (NCS), N-bromosuccinimide (NBS), elementary chlorine, elementary bromine or elementary iodine. These combinations are either used as mixtures or are admixed in situ during reaction.

Examples for $SO_3$ complexes with Lewis bases selected from amines, carboxamides and heteroaromatic compounds containing 1, 2 or 3 basic nitrogen ring atoms are $SO_3$ complexes with trimethylamine, triethylamine, N,N-dimethylaniline, N,N-dimethylformamide, pyridine or polyvinylpyridine. These combinations are either used as mixtures or are admixed in situ during reaction. Expediently, they can be used as commercially available mixtures.

Vilsmeier reagent is the product of the reaction of a formamide ($HC(O)NR_2$, where each R is independently $C_1$-$C_4$-alkyl) with phosphoryl chloride ($P(O)Cl_3$), oxalyl chloride ($ClC(O)—C(O)Cl$) or thionyl chloride ($S(O)Cl_2$), which results in a chloroiminium ion ($ClHC=NR_2^+$). Generally, dimethylformamide is used, i.e. both R are methyl.

One examples for a Lewis acid in the complexes of N,N-dimethylformamide and/or N,N-dimethylacetamide with a Lewis acid is $BF_3$.

The activating agent is more preferably selected from the group consisting of $P(OR^1)_2Cl$, $P(OR^1)Cl_2$, $P(=O)(OR^1)_2Cl$, where each $R^1$ in the three aforementioned compounds is independently $C_1$-$C_4$-alkyl; $PCl_3$, $P(O)Cl_3$, $SO_3$/dimethyl formamide complex, $SOCl_2$, $CH_3S(=O)_2Cl$, CDI and Mitsunobu-type reagents; and in particular from dimethyl chlorophosphite ($P(OCH_3)_2Cl$), diethyl chlorophosphite ($P(OCH_2CH_3)_2Cl$), methyl dichlorophosphite ($P(OCH_3)Cl_2$), ethyl dichlorophosphite ($P(OCH_2CH_3)Cl_2$), $PCl_3$, $P(O)Cl_3$, $SOCl_2$, $CH_3S(=O)_2Cl$ and Mitsunobu-type reagents. More particularly, the activating agent is selected from the group consisting of dimethyl chlorophosphite ($P(OCH_3)_2Cl$), diethyl chlorophosphite ($P(OCH_2CH_3)_2Cl$), methyl dichlorophosphite ($P(OCH_3)Cl_2$), ethyl dichlorophosphite ($P(OCH_2CH_3)Cl_2$), $PCl_3$ and $P(O)Cl_3$. In another more particular embodiment, In another particular embodiment, the activating agent is selected from the group consisting of $P(OR^1)_2Cl$, $P(OR^1)Cl_2$, $P(=O)(OR^1)_2Cl$, where each $R^1$ in the three aforementioned compounds is independently $C_1$-$C_4$-alkyl; $PCl_3$, $P(O)Cl_3$, $SO_3$/dimethyl formamide complex, $CH_3S(=O)_2Cl$ and CDI. In another more particular embodiment, the activating agent is selected from the group consisting of dimethyl chlorophosphite ($P(OCH_3)_2Cl$), diethyl chlorophosphite ($P(OCH_2CH_3)_2Cl$), methyl dichlorophosphite ($P(OCH_3)Cl_2$), ethyl dichlorophosphite ($P(OCH_2CH_3)Cl_2$), $PCl_3$ and $SO_3$/dimethyl formamide complex. Specifically, the activating agent is dimethyl chlorophosphite ($P(OCH_3)_2Cl$), diethyl chlorophosphite ($P(OCH_2CH_3)_2Cl$) or $PCl_3$, and very specifically dimethyl chlorophosphite ($P(OCH_3)_2Cl$) or diethyl chlorophosphite ($P(OCH_2CH_3)_2Cl$).

The compound of the formula 1 and the activating agent are preferably used in a molar ratio of from 10:1 to 1:10, more preferably from 2:1 to 1:5, even more preferably from 1: to 1:4, in particular from 1:1 to 1:3 and specifically from 1:1 to 1:2.

The reaction is preferably carried out in the presence of a solvent. Suitable solvents are polar aprotic solvents, mixtures of polar aprotic solvents and water, $C_1$-$C_4$-alkyl acetates, chlorinated alkanes, aromatic solvents, heterocyclic solvents and mixtures thereof. Although aqueous solvents are generally considered to promote the $S_N1$ path in substitution reactions because they solubilize the generally ionic leaving group, in the present case, mixtures of polar aprotic solvents and water have nevertheless been found to be suitable. In some cases, e.g. if $PCl_3$ is used as activating agent, mixtures of said organic solvents with minor amounts of water may be advantageous.

Polar aprotic solvents are polar solvents without a functional group from which a proton can dissociate. Examples for suitable polar aprotic solvents are amides, such as dimethylformamide (DMF), diethylformamide, dibutylformamide, and dimethylacetamide; cyclic ethers, such as tetrahydrofuran, 2-methyltetrahydrofuran, 1,3-dioxane and 1,4-dioxane; sulfoxides, such as dimethylsulfoxide (DMSO); nitriles, such as acetonitrile; lactams, such as N-methylpyrrolidone (NMP), N-(n-butyl)-pyrrolidone or N-(tert-butyl)pyrrolidone; sulfones, such as sulfolan; carbonic acid esters, such as dimethylcarbonate, ethylenecarbonate or propylene carbonate; lactones, such as γ-butyrolactone or γ-valerolactone; ureas, such as N,N,N',N'-tetramethyl urea, N,N,N',N'-tetrabutyl urea, dimethylpropylene urea (DMPU) or 1,3-dimethyl-2-imidazolinone (DMEU; DMI); and nitro compounds, such as nitromethane.

In mixtures of polar aprotic solvents and water, the mixture contains water in an amount of preferably from 0.5 to 15% by weight, preferably from 1 to 10% by weight, in particular from 1 to 6% by weight, specifically from 1 to 4% by weight, based on the total weight of the mixture.

Examples for suitable $C_1$-$C_4$-alkyl acetates are methyl acetate, ethyl acetate, n-propyl acetate and isopropyl acetate.

Examples for suitable chlorinated alkanes are dichloromethane, trichloromethane or dichloroethane.

Examples for suitable aromatic solvents are benzene, toluene, α,α,α-trifluorotoluene (benzotrifluoride), the xylenes (i.e. 1,2-xylene, 1,3-xylene or 1,4-xylene), fluorobenzene, chlorobenzene, dichlorobenzene or anisole (methoxybenzene).

Examples for suitable heterocyclic solvents are 4-formyl morpholine or dihydrolevoglucosenone (Cyrene®).

More preferably, the solvent is selected from the group consisting of dimethylformamide, diethylformamide, dibutylformamide, dimethylacetamide, tetrahydrofuran, mixtures of tetrahydrofuran and water (e.g. containing water in an amount of from 0.5 to 15% by weight, preferably from 1 to 10% by weight, in particular from 1 to 6% by weight, specifically from 1 to 4% by weight, based on the total weight of the THF/water mixture), 2-methyltetrahydrofuran, the dioxanes (i.e. 1,3-dioxane and 1,4-dioxane), dimethylsulfoxide, acetonitrile, N-methylpyrrolidone, N-(n-butyl)-pyrrolidone, N-(tertbutyl)-pyrrolidone, sulfolane, dimethylcarbonate, diethylcarbonate, propylene carbonate, γ-valerolactone, N,N,N',N'-tetrabutyl urea, 1,3-dimethyl-2-imidazolinone, ethyl acetate, isopropyl acetate, dichloromethane, trichloromethane, dichloroethane, benzene, toluene, trifluorotoluene, the xylenes, chlorobenzene, dichlorobenzene, 4-formylmorpholine, dihydrolevoglucosenone (Cyrene®) and mixtures thereof. In particular the solvent is selected from the group consisting of dimethylformamide, diethylformamide, dibutylformamide, dimethylacetamide, tetrahydrofuran, mixtures of tetrahydrofuran and water (e.g. containing water in an amount of from 0.5 to 15% by weight, preferably from 1 to 10% by weight, in particular from 1 to 6% by weight, specifically from 1 to 4% by weight, based on the total weight of the THE/water mixture), 2-methyltetrahydrofuran, 1,4-dioxane, acetonitrile, ethyl acetate, dichloromethane, toluene, chlorobenzene and mixtures thereof; specifically from dimethylformamide, dimethylacetamide, tetrahydrofuran, 2-methyltetrahydrofuran, acetonitrile, dichloromethane, toluene and mixtures thereof and very specifically from tetrahydrofuran, 2-methyltetrahydrofuran, acetonitrile, dichloromethane, toluene and mixtures thereof.

In a particular embodiment, the reaction is carried out in the presence of a base. The base is preferably selected from the group consisting of alkali metal hydroxides, amines of the formula $NR^1R^2R^3$, where $R^1$, $R^2$ and $R^3$, independently of each other, are selected from the group consisting of hydrogen, $C_1$-$C_6$-alkyl, $C_3$-$C_6$-cycloalkyl, $C_1$-$C_4$-alkoxy and $C_1$-$C_4$-alkoxy-$C_1$-$C_4$-alkyl, where at least one of $R^1$, $R^2$ and $R^3$ is not hydrogen; diamines of the formula $NR^1R^2$-A-$NR^3R^4$, where $R^1$, $R^2$, $R^3$ and $R^4$, independently of each other, are selected from the group consisting of hydrogen, $C_1$-$C_6$-alkyl, $C_3$-$C_6$-cycloalkyl, $C_1$-$C_4$-alkoxy and $C_1$-$C_4$-alkoxy-$C_1$-$C_4$-alkyl, and A is $(CH_2)_2$ or $(CH_2)_3$; and a 5- or 6-membered saturated heterocyclic ring containing one nitrogen atom as ring member and optionally one further heteroatom selected from N and O as ring member, where the ring may carry 1 to 6 $C_1$-$C_4$-alkyl groups and/or 1 or 2 OH groups. In particular, the base is selected from the group consisting of LiOH, NaOH, KOH, diethylamine, triethylamine, tributylamine, diisopropylethylamine, dimethylisopropylamine, ethyl-tert-butylamine, isopropyl-tert-butylamine, (2-methoxyethyl)methylamine, N,N-dicyclohexylmethylamine, N-cyclohexyldimethylamine, N,N,N',N'-tetramethylethylenediamine, N,N,N',N'-tetramethylpropylene-1,3-diamine, piperdine, N-methylpiperidine, 2,2,6,6-tetramethylpiperidine, N-methyl-2,6,6-tetramethylpiperidine, N-methyl-4-hydroxy-2,2,6,6-tetramethylpiperidine, morpholine and N-methylmorpholine, where the bases can be used in supported from (i.e. on a support material); and specifically from triethylamine, tributylamine and diisopropylethylamine.

Suitable support materials for bases/supported bases are for example silica ($SiO_2$) and organic polymers, such as polystyrene or acrylic ester based supports, for example polymers typically used in ion exchange resins, such as styrene (co)polymers containing sulfonic acid groups, specifically styrene-divinyl benzene copolymers containing sulfonic acid groups. Commercial examples for such ion exchanger supports are materials commercialized under the Lewatit® (Lanxess), Purolite® (The Purolite Company), Dowex® (Dow Chemical Company), Amberlite® (Rohm and Haas Company) or Amberlyst® (Rohm and Haas Company) brands.

In another particular embodiment, the reaction is carried out without a base. "Without a base" or "in the absence of a base" in this context means without an additional base, i.e. a base which is different from the mandatory reactants. For instance, some activators contain basic components, such as the amines or heteroaromatic compounds in the $SO_3$ complexes with Lewis bases.

The reaction is carried out at a temperature of preferably from −80 to 120° C., more preferably from −20 to 100° C., and in particular from −10 to 90° C.

The reaction time depends on various factors, such as the reaction temperature, the concentration of the reactants in the reaction mixture and the like. Typically, it is in the range of from about 15 min to 48 h, preferably from 1 to 10 h.

The reaction is generally carried out by mixing the compound 1 and the activating agent, typically in a solvent. Preferably, the activating agent is added to a solution of compound 1 in a solvent. Depending on the activating agent used, it can be expedient to add the agent to a solution of compound 1 cooled to −80 to 10° C., e.g. to −20 to 0° C., and warm the reaction mixture only after completion of addition if a higher reaction temperature than the temperature at addition is desired. Depending on the reactivity of the activating agent, it can be expedient to add the latter gradually (continuously or portion-wise) to avoid heat development. The reactivity is not only dependent from the type of activating agent, but also from its state after storage, so that preliminary tests are expedient.

Reverse addition (i.e. addition of the compound 1 to a solution of the activating agent) is however also possible.

In a preferred embodiment, the method of the invention serves for preparing (3R)-3-(2-chlorothiazol-5-yl)-8-methyl-7-oxo-6-phenyl-2,3-dihydrothiazolo[3,2-a]pyrimidin-4-ium-5-olate of the formula (I-R)

(I-R)

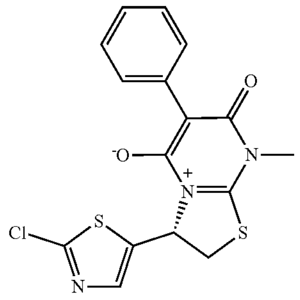

in an enantiomeric excess of at least 55% ee, preferably at least 60% ee, more preferably at least 70% ee, in particular at least 80% ee and specifically at least 90% ee.

To this purpose, 2-[(2S)-2-(2-chlorothiazol-5-yl)-2-hydroxy-ethyl]sulfanyl-6-hydroxy-3-methyl-5-phenyl-pyrimidin-4-one of the formula 1-S

1-S

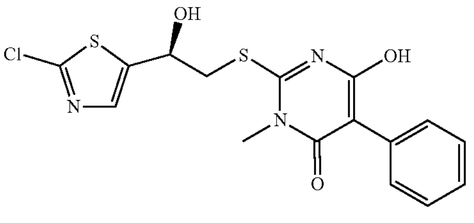

with an enantiomeric excess of at least 55% ee, preferably at least 60% ee, more preferably at least 70% ee, in particular at least 80% ee and specifically at least 90% ee or a tautomer thereof or a mixture of different tautomers thereof is reacted with an activating agent as described above. The intramolecular nucleophilic attack proceeds predominantly from the reverse side to the OH leaving group, and thus with inversion of configuration at the asymmetric carbon atom (given that nucleophile and nucleofuge have the same priority according to the Cahn-Ingold-Prelog rules, the absolute configuration also changes from S to R).

All remarks made above to suitable reaction conditions apply here analogously.

In another preferred embodiment, the method of the invention serves for preparing (3S)-3-(2-chlorothiazol-5-yl)-8-methyl-7-oxo-6-phenyl-2,3-dihydrothiazolo[3,2-a]pyrimidin-4-ium-5-olate of the formula (1-S)

(I-S)

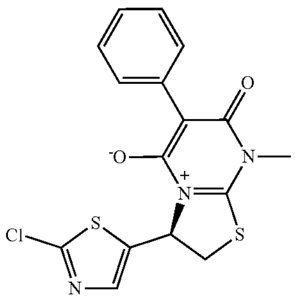

in an enantiomeric excess of at least 55% ee, preferably at least 60% ee, more preferably at least 70% ee, in particular at least 80% ee and specifically at least 90% ee.

To this purpose, 2-[(2R)-2-(2-chlorothiazol-5-yl)-2-hydroxy-ethyl]sulfanyl-6-hydroxy-3-methyl-5-phenyl-pyrimidin-4-one of the formula 1-R

1-R

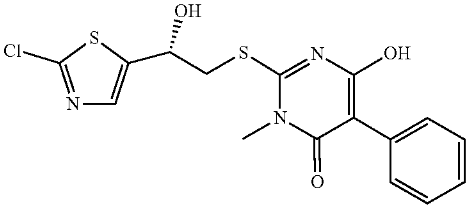

with an enantiomeric excess of at least 55% ee, preferably at least 60% ee, more preferably at least 70% ee, in particular at least 80% ee and specifically at least 90% ee or a tautomer thereof or a mixture of different tautomers thereof is reacted with an activating agent as described above. The intramolecular nucleophilic attack proceeds predominantly from the reverse side to the OH leaving group, and thus with inversion of configuration at the asymmetric carbon atom (given that nucleophile and nucleofuge have the same priority according to the Cahn-Ingold-Prelog rules, the absolute configuration also changes from R to S).

All remarks made above to suitable reaction conditions apply here analogously.

After completion of the reaction, the pyrimidinone of the formula (I) in enantiomerically enriched form is generally isolated from the reaction mixture. Isolation typically comprises steps suitable for precipitating the compound (I). For instance, the solvent can be partially removed, optionally under reduced pressure, upon which the desired compound (I) precipitates. Depending on the temperature applied for partially removing the solvent, on the amount of solvent removed and of course on the nature of the solvent, it might be expedient to cool the residual mixture, where cooling can occur continually or stepwise. Alternatively or additionally, a further solvent in which compound (I) has low solubility can be added, expediently after partial removal of the reaction solvent, upon which compound (I) precipitates; as the case may be after cooling (again continually or stepwise). Suitable solvents in which compound (I) has low solubility are for example aromatic hydrocarbons, such as benzene, toluene, trifluorotoluene, the xylenes (i.e. 1,2-xylene, 1,3-xylene or 1,4-xylene), chlorobenzene or dichlorobenzene; $C_1$-$C_4$-alkyl acetates, such as methyl acetate, ethyl acetate, n-propyl acetate and isopropyl acetate; $C_1$-$C_4$-alkanols, such as methanol, ethanol, n-propanol, isopropanol, n-butanol, sec-butanol, isobutanol and tert-butanol; glycols, such as ethylene glycol, propylene glycol, diethylene glycol and triethylene glycol; glycerol, water or mixtures of the aforementioned solvents.

The precipitate can be isolated by usual methods, such as filtration, centrifugation, sedimentation and removal of the supernatant etc., where filtration is preferred. The filter cake can be further purified by washing with suitable solvents, such as the above-listed solvent with low solubility for compound (I).

The compound 1 in enantiomerically enriched form is obtainable, for example, by asymmetric transfer hydrogenation of 2-[2-(2-chlorothiazol-5-yl)-2-oxo-ethyl]sulfanyl-6-hydroxy-3-methyl-5-phenyl-pyrimidin-4-one with formic acid or a formate as reduction agent in the presence of a chiral transition metal complex. This reaction is described in detail in EP application no. 21153034.0.

2-[2-(2-Chlorothiazol-5-yl)-2-oxo-ethyl]sulfanyl-6-hydroxy-3-methyl-5-phenyl-pyrimidin-4-one is in turn obtainable, for example, by reaction of N-methylthiourea with an alkyl 2-phenylmalonate to 6-hydroxy-3-methyl-5-phenyl-2-sulfanyl-pyrimidin-4-one or the corresponding thiolate and reaction thereof with 2-chloro-1-(2-chlorothiazol-5-yl)ethanone. This reaction is described in detail in EP application no. 21153040.7.

N-methylthiourea and alkyl 2-phenylmalonates are commercially available. 2-Chloro-1-(2-chlorothiazol-5-yl)ethanone can be prepared, for example, as described in WO 2018/197541 or WO 2018/202654 by reaction of 2-chlorothiazole with a Grignard reagent to the corresponding chloro-(2-chlorothiazol-5-yl) magnesium species and reaction thereof with 2-chloro-N-methoxy-N-methyl-acetamide. Alternatively, the compound 3 can be prepared from thiourea according the method described by T. Chalopin et al. in Org. Biomol. Chem., 2016, 14, 3913-3925.

The present method leads to the compound (I) in high yields and high stereoselectivity.

The invention relates moreover to 2-[2-(2-chlorothiazol-5-yl)-2-hydroxy-ethyl]sulfanyl-6-hydroxy-3-methyl-5-phenyl-pyrimidin-4-one 1

1

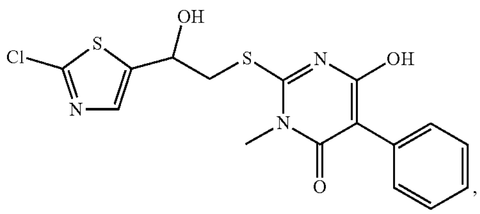, to a tautomer thereof or a mixture of different tautomers thereof and to enantiomerically enriched forms thereof. This formula 1 and the formula 1 depicted in context with the method of the invention are equivalent; the formula 1 depicted in context with the method of the invention shows however more clearly the stereogenic center of the molecule.

In particular, the invention relates to 2-[(2S)-2-(2-chlorothiazol-5-yl)-2-hydroxyethyl]sulfanyl-6-hydroxy-3-methyl-5-phenyl-pyrimidin-4-one of the formula 1-S

1-S

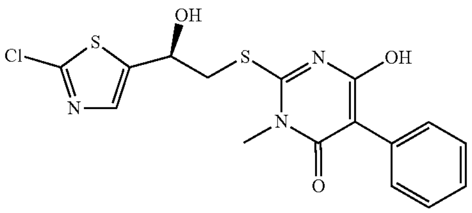

in enantiomeric excess, preferably in an enantiomeric excess of at least 55% ee, more preferably of at least 60% ee, even more preferably of at least 70% ee, in particular of at least 80% ee and specifically of at least 90% ee; and to a tautomer or a mixture of different tautomers thereof.

In another particular embodiment, the invention relates to 2-[(2R)-2-(2-chlorothiazol-5-yl)-2-hydroxy-ethyl]sulfanyl-6-hydroxy-3-methyl-5-phenyl-pyrimidin-4-one of the formula 1-R

1-R

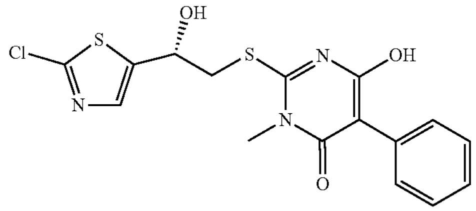

in enantiomeric excess, preferably in an enantiomeric excess of at least 55% ee, more preferably of at least 60% ee, even more preferably of at least 70% ee, in particular of at least 80% ee and specifically of at least 90% ee; and to a tautomer or a mixture of different tautomers thereof.

The invention relates also to the use of 2-[2-(2-chlorothiazol-5-yl)-2-hydroxyethyl]sulfanyl-6-hydroxy-3-methyl-5-phenyl-pyrimidin-4-one 1 or of its tautomer or of a mixture of different tautomers thereof or of enantiomerically enriched forms thereof as intermediate in the preparation of 2,3-dihydrothiazolo[3,2-a]pyrimidinium compounds, specifically of 3-(2-chlorothiazol-5-yl)-8-methyl-7-oxo-6-phenyl-2,3-dihydrothiazolo[3,2-a]pyrimidin-4-ium-5-olate (1) and enantiomerically enriched forms thereof.

The present invention is further illustrated in the following examples.

EXAMPLES

Methods

The compounds were characterized was by coupled High Performance Liquid Chromatography/mass spectrometry (HPLC/MS), by NMR or by melting points.

HPLC method: Agilent Eclipse XDB-C18, 150 mm×4.6 mm ID×5 µm

Gradient A=0.5% $H_2SO_4$ in water, B=acetonitrile

Flow=1.1 mL/min, column oven temperature=30° C.

Gradient program=20% B–100% B–15 min

Run Time=15 min

Chiral HPLC method: Agilent Series 1260, Chiralpak AD-RH 5 µm 150*4.6 mm

Gradient A=0.1% $H_3PO_4$ in water, B=acetonitrile/2-propanol (1:1).

Flow=1.2 mL/min, column oven temperature=50° C.

Gradient program

| t [min] | % B | flow [mL/min] |
|---|---|---|
| 0 | 30 | 1.2 |
| 10 | 50 | 1.2 |
| 15 | 100 | 1.2 |
| 20 | 100 | 1.2 |
| 20.1 | 50 | 1.2 |

Run Time=25 min

LCMS method 1: C18 Column (50 mm×2.1 mm×1.7 µm)

Gradient A=0.1% TFA in water, B=acetonitrile

Flow=0.8 mL/min to 1.0 mL/min in 1.5 min, column oven temperature=60° C.

Gradient program=10% B to 100% B in 15 min, hold for 1 min 100% B, 1 min–10% B

Run time: 1.75 min $^1$H-NMR: The signals are characterized by chemical shift (ppm) vs. tetramethylsilane, by their multiplicity and by their integral (relative number of hydrogen atoms given). The following abbreviations are used to characterize the multiplicity of the signals: m=multiplet, q=quartet, t=triplet, d=doublet, s=singlet, dd=doublet of doublets.

Abbreviations used are: t for time, h for hour(s), min for minute(s), rt for retention time, r.t. for room temperature (20-25° C.), TFA for trifluoroacetic acid.

TsDPEN is a bidentate ligand of the following formula:

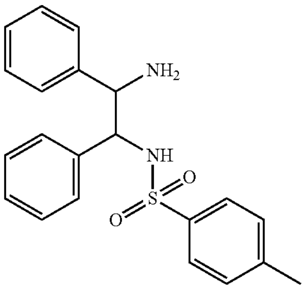

TsDPEN (1S,2S)-TsDPEN is the 1S,2S form of TsDPEN and (1R,2R)-TsDPEN is the 1R,2R form of TsDPEN. Positions 1 and 2 relate to the two carbon atoms carrying the phenyl rings and the (substituted) amino groups.

Example 1: Preparation of (3S)-3-(2-chlorothiazol-5-yl)-8-methyl-7-oxo-6-phenyl-2,3-dihydrothiazolo[3,2-a]pyrimidin-4-ium-5-olate

1.1 Preparation of 2-[2-(2-chlorothiazol-5-yl)-2-oxo-ethyl]sulfanyl-6-hydroxy-3-methyl-5-phenyl-pyrimidin-4-one In a 20 L jacketed reactor, a solution of N-methylthiourea (778 g, 8.38 mol) and $NaOCH_3$ (1584 g, 8.79 mol, 30 wt % solution in methanol) and methanol (384 g, 12 mol) under $N_2$ was warmed to an internal temperature of 65° C. Then diethyl 2-phenylmalonate (2121 g, 8.79 mol) was dosed over 30 min, and the pump was washed with methanol (384 g, 12 mol). The reaction was then stirred for 4 h at an internal temperature of 65° C., and then for 18 h at 50° C. Over this time a suspension formed. Then a solution of 2-chloro-1-(2-chlorothiazole-5-yl)ethanone (1859 g, 9.00 mol) in ethanol (8.050 g, 175 mol) was dosed over 30 min. The reaction was stirred 75 min at 50° C., and a large precipitation of solid occurred. At this point ethanol (2.300 g, 50 mol) was added, and the stirring speed was increased. The reaction was stirred at 50° C. a further 36 h and then reaction was then cooled to 20° C. over 16 h. The formed solid was then isolated via filtration in three 4 L fritted funnels. Each filtercake was washed with 500 mL of ethanol. The filtercake was then returned to the 20 L reactor and slurried with 15 L of water at 75° C. for 1 h. The slurry was then filtered in two 4 L fritted funnels, and each filtercake washed three times with 500 mL of room temperature water, and then dried at 80° C. and 5 mbar in a vacuum drying oven. After drying 3040 g (91%) of the title compound in form of a brown solid in 99 wt % purity were isolated.

$^1H$ NMR (400 MHz, DMSO-d6): δ=8.75 (s, 1H), 7.15-7.45 (m, 5H), 4.9 (s, 2H), 3.46 (s, 3H).

1.2 Preparation of 2-[(2R)-2-(2-chlorothiazol-5-yl)-2-hydroxy-ethyl]sulfanyl-6-hydroxy-3-methyl-5-phenyl-pyrimidin-4-one (1-R)

A solution of 2-[2-(2-chlorothiazol-5-yl)-2-oxo-ethyl]sulfanyl-6-hydroxy-3-methyl-5-phenyl-pyrimidin-4-one (20.0 g, 50.4 mmol, 99% purity, 1.00 eq) and 158.3 g dimethyl acetamide was cooled to −5° C., and a sparge of nitrogen was turned on (dip-tube, 13 Nl/h). 6.0 g of a formic acid (1.54 eq)/diisopropylethylamine (0.375 eq) mixture (molar ratio 4.1:1) were added, followed by a solution of the preformed catalyst Rh(III)ClCp* (1R,2R-TsDPEN) (obtained by reacting $[Rh(III)Cl_2Cp^*]_2$ with 1R,2R-TsDPEN) (0.340 g, 0.501 mmol, 94% purity) in 10 g dimethyl acetamide. The reaction mixture was stirred for 2 h and then $H_2SO_4$ (10 g, 100 mmol, 98% purity) was dosed over 2 h, maintaining an internal temperature <0° C. The pressure on the reactor was reduced to 5 mbar and the temperature on the mantel increased to 57° C. to remove 117 g of dimethyl acetamide via distillation. 178 g of 2-methyltetrahydrofuran and 100 g of water were then added to the reactor. The two phases formed were homogenized for 15 min, and then allowed to separate. The bottom aqueous phase was removed from the reactor. 100 g of water and 2 g $H_2SO_4$ were added to the reactor. The two phases were homogenized for 15 min and then allowed to separate. The bottom aqueous phase and the organic phase were removed separately from the reactor. The combined aqueous phases were returned to the reactor with the addition of 170 g of 2-methyltetrahydrofuran. The two phases were homogenized for 15 min and then allowed to separate. The bottom aqueous phase was removed from the reactor. The 2-methyltetrahydrofuran phases were then returned to the reactor, the pressure was reduced to 350 mbar, and the mantel set at 59° C. to remove water azeotropically via a Dean-Stark trap until <200 ppm water remained in the 2-methyltetrahydrofuran phase. Removal of 2-methyltetrahydrofuran phase gave the title product in 85% yield and 95% ee.

$^1H$ NMR (400 MHz, DMSO-d6): δ=11.15 (s, 1H), 7.7 (s, 1H), 7.18-7.47 (m, 5H), 6.5 (s, 1H), 5.2 (m, 1H), 3.72 (dd, 1H), 3.54 (dd, 1H), 3.4 (s, 3H).

1.3 Preparation of (3S)-3-(2-chlorothiazol-5-yl)-8-methyl-7-oxo-6-phenyl-2,3-dihydrothiazolo[3,2-a]pyrimidin-4-ium-5-olate (1-S)

4.67 g of 2-[(2R)-2-(2-chlorothiazol-5-yl)-2-hydroxy-ethyl]sulfanyl-6-hydroxy-3-methyl-5-phenyl-pyrimidin-4-one (90%, 95% ee, 1.00 eq) were dissolved in 18.7 g of acetonitrile and cooled to 0° C. 2.64 g (95%, 1.5 eq) of diethyl chlorophosphite were dosed in 2 h and the mixture was stirred for 2.5 h. After warming to room temperature and stirring for 1 h, the mixture was treated with 18.7 g of toluene. The suspension was concentrated 3 times at 50° C. while adding more toluene. The suspension was cooled to 0° C., the solid filtered off and washed with toluene 2×. After drying (90° C., 2 h, <10 mbar), 3.46 g (99% ee, 99%, 84% yield) of the title compound was obtained as an off-white to beige solid.

$^1H$ NMR (400 MHz, DMSO-d6): δ=7.96 (s, 1H), 7.6 (d, J=7.5 Hz, 1H), 7.21-7.26 (m, 2H), 7.06-7.11 (m, 1H), 6.48 (d, J=8.1 Hz, 1H), 4.25-4.32 (m, 1H), 3.94 (d, J=12 Hz, 1H), 3.42, (s, 3H).

m/z $(M+H^+)$=378

Example 2: Preparation of (3R)-3-(2-chlorothiazol-5-yl)-8-methyl-7-oxo-6-phenyl-2,3-dihydrothiazolo[3,2-a]pyrimidin-4-ium-5-olate

2.1 Preparation of 2-[(2S)-2-(2-chlorothiazol-5-yl)-2-hydroxy-ethyl]sulfanyl-6-hydroxy-3-methyl-5-phenyl-pyrimidin-4-one (1-S)

A solution of 2-[2-(2-chlorothiazol-5-yl)-2-oxo-ethyl]sulfanyl-6-hydroxy-3-methyl-5-phenyl-pyrimidin-4-one (22.8 g, 49.2 mmol, 85% purity, 1.00 eq) and 160 g dimethyl formamide was cooled to 3° C., and a sparge of nitrogen was turned on. A solution of the preformed catalyst Rh(III)ClCp* (1S,2S-TsDPEN) (obtained by reacting $[Rh(III)Cl_2Cp^*]_2$ with 1S,2S-TsDPEN) (0.99 g, 1.48 mmol, 95% purity) in 21 g dimethyl formamide was added, followed by 5.3 g of a formic acid (1.53 eq)/triethylamine (0.37 eq) mixture (molar ratio 4.1:1). After 60 min, the reaction mixture was quenched with 38 mL of HCl in methanol (1 M). This mixture was slowly added to cold water and the resulting precipitate was filtered off. The solid was redisolved in 1000 g ethyl acetate and treated with 11 g charcoal and magnesium sulfate. After 20 min, the suspension was filtered and the filtercake was washed with ethyl acetate (2×200 g). Evaporation of the solvent yielded 19.3 g of the title compound (90%, 96% ee).

2.2 Preparation of (3R)-3-(2-chlorothiazol-5-yl)-8-methyl-7-oxo-6-phenyl-2,3-dihydrothiazolo[3,2-a]pyrimidin-4-ium-5-olate (I-R)

4.67 g of 2-[(2S)-2-(2-chlorothiazol-5-yl)-2-hydroxy-ethyl]sulfanyl-6-hydroxy-3-methyl-5-phenyl-pyrimidin-4-one (90%, 95% ee, 1.00 eq) were dissolved in 18.7 g of acetonitrile and cooled to 0° C. 2.64 g (95%, 1.5 eq) of diethyl chlorophosphite were dosed in 2 h and the mixture was stirred for 2.5 h. After warming to room temperature and stirring for 1 h, the mixture was treated with 18.7 g of toluene. The suspension was concentrated 3 times at 50° C. while adding more toluene. The suspension was cooled to 0° C., the solid filtered off and washed with toluene 2×. After drying (90° C., 2 h, <10 mbar), 3.46 g (99% ee, 99%, 84% yield) of the title compound was obtained as an off-white to beige solid.

$^1H$ NMR (400 MHz, DMSO-d6): δ=7.96 (s, 1H), 7.6 (d, J=7.5 Hz, 1H), 7.21-7.26 (m, 2H), 7.06-7.11 (m, 1H), 6.48 (d, J=8.1 Hz, 1H), 4.25-4.32 (m, 1H), 3.94 (d, J=12 Hz, 1H), 3.42, (s, 3H).

m/z $(M+H^+)$=378

Example 3: Preparation of (3R)-3-(2-chlorothiazol-5-yl)-8-methyl-7-oxo-6-phenyl-2,3-dihydrothiazolo[3,2-a]pyrimidin-4-ium-5-olate (I-R)

0.33 g of 2-[(2S)-2-(2-chlorothiazol-5-yl)-2-hydroxy-ethyl]sulfanyl-6-hydroxy-3-methyl-5-phenyl-pyrimidin-4-one (96%, 96% ee, 1.00 eq) were dissolved in 8.6 mL of tetrahydrofuran. 0.18 mL (97%, 2.5 eq) of phosphorus trichloride were added and the mixture was stirred overnight. After warming to 40° C. for 2 h, the mixture was treated with 8.7 g of sodium bicarbonate solution (8%) and 5 g of ethyl acetate. The phases were separated and the aqueous layer was extracted 2× with ethyl acetate. The organic phases were combined and washed with water. The organic phase was 3 times partially evaporated at 50° C. The suspension was cooled to 0° C., the solid filtered off and washed with ethyl acetate 2×. After drying (90° C., 2 h, <10 mbar), 0.22 g (>99% ee, 98%, 70% yield) of the title compound was obtained as an off-white to beige solid.

Example 4: Preparation of (3R)-3-(2-chlorothiazol-5-yl)-8-methyl-7-oxo-6-phenyl-2,3-dihydrothiazolo[3,2-a]pyrimidin-4-ium-5-olate (I-R)

5.12 g of 2-[(2S)-2-(2-chlorothiazol-5-yl)-2-hydroxy-ethyl]sulfanyl-6-hydroxy-3-methyl-5-phenyl-pyrimidin-4-one (87%, 95% ee, 1.00 eq) were dissolved in 34 mL of methyltetrahydrofuran and the solution was cooled to 0° C. 2.55 mL (95%, 1.7 eq) of diethyl chlorophosphite were added and the mixture was stirred for 6 h at 0° C. and overnight at room temperature. After warming to 40° C. for 1 h, the suspension was cooled to 0° C., the solid filtered off and washed with ethyl acetate 2×. After drying (90° C., 2 h, <10 mbar), 3.65 g (99% ee, 97%, 87% yield) of the title compound was obtained as an off-white to beige solid.

Example 5: Preparation of either racemic or (3R)-3-(2-chlorothiazol-5-yl)-8-methyl-7-oxo-6-phenyl-2,3-dihydrothiazolo[3,2-a]pyrimidin-4-ium-5-olate Using Various Reaction Conditions Ca. 30 mg of either racemic 2-[2-(2-chlorothiazol-5-yl)-2-hydroxy-ethyl]sulfanyl-6-hydroxy-3-methyl-5-phenyl-pyrimidin-4-one (>98%, 1.00 eq) or of 2-[(2S)-2-(2-chlorothiazol-5-yl)-2-hydroxy-ethyl]sulfanyl-6-hydroxy-3-methyl-5-phenyl-pyrimidin-4-one (>98%, 95% ee, 1.00 eq) were dissolved in 2 mL of solvent and cooled/heated to the respective temperature. 2.50 eq of activating agent AA were added and the mixture was stirred for the indicated time. An aliquot of the mixture was quenched with HCl/methanol to determine the conversion to 3-(2-chlorothiazol-5-yl)-8-methyl-7-oxo-6-phenyl-2,3-dihydrothiazolo[3,2-a]pyrimidin-4-ium-5-olate (in case of using the S-enantiomer of the starting compound: conversion to (3R)-3-(2-chlorothiazol-5-yl)-8-methyl-7-oxo-6-phenyl-2,3-dihydrothiazolo[3,2-a]pyrimidin-4-ium-5-olate) by qualitative HPLC. The reaction conditions and the area-% of the title product in the HPLC chromatogram are compiled in the following table. Where the starting compound was used in form of its S-enantiomer, the enantioselectivity of the R-enantiomer of the title compound (I-R) is given as % ee.

| AA | Solvent | Conditions | HPLC area-% of (I) | % ee (I-R) |
|---|---|---|---|---|
| $PCl_3$ | $CH_3CN$ | 25° C., 16 h | 90 | — |
| $(EtO)_2PCl$ | $CH_3CN$ | 25° C., 16 h | 98 | — |
| $MeOPCl_2$ | $CH_3CN$ | 25° C., 16 h | 98 | — |
| $EtOPCl_2$ | $CH_3CN$ | 25° C., 16 h | 98 | — |
| $(EtO)_2P(O)Cl$ | $CH_3CN$ | 25° C., 16 h | 97 | — |
| $(MeO)_2P(O)Cl$ | $CH_3CN$ | 25° C., 16 h | | |
| $P(O)Cl_3$ | $CH_3CN$ | 25° C., 16 h | | |
| $PCl_3$ | $CH_2Cl_2$ | 25° C., 2 h | 100 | — |
| $(EtO)_2PCl$ | $CH_2Cl_2$ | 25° C., 2 h | 100 | — |
| $MeOPCl_2$ | $CH_2Cl_2$ | 25° C., 2 h | 93 | — |
| $EtOPCl_2$ | $CH_2Cl_2$ | 25° C., 2 h | 77 | — |
| PPA | $CH_2Cl_2$ | 25° C., 17 h | | |
| $P_4O_{10}$ | $CH_2Cl_2$ | 25° C., 17 h | | |
| $SO_3$*Pyr | $CH_2Cl_2$ | 25° C., 17 h | | |
| $SO_3$*$NEt_3$ | $CH_2Cl_2$ | 25° C., 17 h | | |
| $SO_3$*DMF | $CH_2Cl_2$ | 25° C., 17 h | 92 | — |
| $PPh_3$/NCS | $CH_2Cl_2$ | 25° C., 23 h | | |
| $PPh_3$/DEAD | $CH_2Cl_2$ | 25° C., 23 h | | |
| $PPh_3$/DIAD | $CH_2Cl_2$ | 25° C., 23 h | | |
| CMDMC + TEA | $CH_2Cl_2$ | 25° C., 24 h | | |
| CMDMC | $CH_2Cl_2$ | 25° C., 24 h | | |
| DMF-DMA/$BF_3$ | $CH_2Cl_2$ | 25° C., 24 h | | |
| $PCl_3$ | MTBE | 25° C., 16 h | | |
| $PCl_3$ | Toluene | 25° C., 16 h | | |
| $PCl_3$ | Dioxan | 25° C., 16 h | 100 | — |
| $PCl_3$ | Chlorobenzene | 25° C., 16 h | 93 | — |
| $PCl_3$ | THF | 25° C., 16 h | 97 | — |
| $PCl_3$ | THF/$H_2O$ (1 eq[1]) | 25° C., 2 h | 95 | — |
| $PCl_3$ | THF/$H_2O$ (1.5 eq[1]) | 25° C., 2 h | 95 | — |
| $PCl_3$ | THF/$H_2O$ (2 eq[1]) | 25° C., 2 h | 95 | — |
| $PCl_3$ | THF/$H_2O$ (2.5 eq[1]) | 25° C., 2 h | 94 | — |
| $PCl_3$ | Ethyl acetate | 25° C., 16 h | 100 | — |
| $PCl_3$ | $CH_2Cl_2$ | −15° C., 6 h | | |

-continued

| AA | Solvent | Conditions | HPLC area-% of (I) | % ee (I-R) |
|---|---|---|---|---|
| $PCl_3$ | $CH_2Cl_2$ | 25° C., 19 h | 100 | 93 |
| $PCl_3$ | $CH_2Cl_2$ | 0° C., 24 h | 100 | 93 |
| $(EtO)_2PCl$ | $CH_2Cl_2$ | 0° C., 24 h | 100 | 96 |
| $MeOPCl_2$ | $CH_2Cl_2$ | 0° C., 24 h | | |
| $EtOPCl_2$ | $CH_2Cl_2$ | 0° C., 24 h | 81 | 93 |
| $MeOPCl_2$ | $CH_3CN$ | 0° C., 24 h | 100 | 89 |
| $MeOPCl_2$ | THF | 0° C., 24 h | | |
| $SO_3$*DMF | $CH_2Cl_2$ | 25° C., 24 h | 72 | 93 |
| $(EtO)_2PCl$ | Me—THF | 0° C., 24 h | 87 | 99 |
| $(EtO)_2PCl$ | Toluene | 30° C., 24 h | 87 | 98 |

Me = methyl;
Et = ethyl;
Ph = phenyl;
PPA = polyphosphoric acid;
Pyr = pyridine;
DMF = dimethylformamide;
DMA = dimethylamide;
NCS = N-chlorosuccinimide;
CMDMC = Vilsmeyer reagent; (chloromethylene)-N,N-dimethyliminium chloride ($CHCl{=}N(CH_3)_2^+Cl^-$);
TEA = triethylamine;
MTBE = methyl tert-butyl ether;
THF = tetrahydrofuran;
Me—THF = 2-methyltetrahydrofuran
[1] in this context, 1 eq is the weight equivalent to the starting compound; i.e. 30 mg.

Example 6: Preparation of racemic 3-(2-chlorothiazol-5-yl)-8-methyl-7-oxo-6-phenyl-2,3-dihydrothiazolo[3,2-a]pyrimidin-4-ium-5-olate 129 mg (0.326 mmol, 1.0 eq) of racemic 2-[2-(2-chlorothiazol-5-yl)-2-hydroxyethyl]sulfanyl-6-hydroxy-3-methyl-5-phenyl-pyrimidin-4-one was suspended in acetonitrile (2 mL) and cooled to 0° C. Then a solution of 132 mg (0.814 mmol, 2.5 eq) CDI (carbonyldiimidazole) in acetonitrile (2 mL) was added. Over 3d in total, the reaction mixture was gradually warmed up to 45° C. The reaction mixture was quenched with water and acetonitrile to obtain 11.84 g of a solution containing 89 mg (0.234 mmol, 72% yield) of the title product.

Example 7: Preparation of racemic 3-(2-chlorothiazol-5-yl)-8-methyl-7-oxo-6-phenyl-2,3-dihydrothiazolo[3,2-a]pyrimidin-4-ium-5-olate 117 mg (0.296 mmol, 1.0 eq) of racemic 2-[2-(2-chlorothiazol-5-yl)-2-hydroxyethyl]sulfanyl-6-hydroxy-3-methyl-5-phenyl-pyrimidin-4-one was suspended in acetonitrile (2 mL) and cooled to 0° C. 75 mg (0.742 mmol, 2.5 eq) of triethyl amine and 91 mg (0.592 mmol, 2.0 eq) of $POCl_3$ were successively added. The reaction mixture was stirred over night at 0° C. The reaction mixture was diluted with acetonitrile to obtain 3.62 g of a solution containing 72 mg (0.192 mmol, 65% yield) of the title product.

Example 8: Preparation of racemic 3-(2-chlorothiazol-5-yl)-8-methyl-7-oxo-6-phenyl-2,3-dihydrothiazolo[3,2-a]pyrimidin-4-ium-5-olate 100 mg (0.253 mmol, 1.0 eq) racemic 2-[2-(2-chlorothiazol-5-yl)-2-hydroxyethyl]sulfanyl-6-hydroxy-3-methyl-5-phenyl-pyrimidin-4-one was suspended in acetonitrile (2 mL) and cooled to 0° C. 74 mg of triethyl amine (0.731 mmol, 2.9 eq) and 78 mg of methanesulfonyl chloride (0.681 mmol, 2.7 eq) were successively added. The reaction mixture was stirred over two days at 0° C. The reaction mixture was diluted with acetonitrile to obtain 6.22 g of a solution containing 61 mg (0.161 mmol, 64% yield) of the title product.

The invention claimed is:

1. A method for preparing an enantiomerically enriched form of 3-(2-chlorothiazol-5-yl)-8-methyl-7-oxo-6-phenyl-2,3-dihydrothiazolo[3,2-a]pyrimidin-4-ium-5-olate of formula (I):

(I)

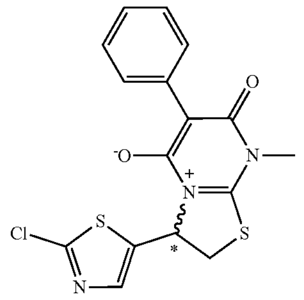

where the asterisk * shows the stereogenic center;

which method comprises reacting an enantiomerically enriched form of 2-[2-(2-chlorothiazol-5-yl)-2-hydroxy-ethyl]sulfanyl-6-hydroxy-3-methyl-5-phenyl-pyrimidin-4-one of formula 1

1

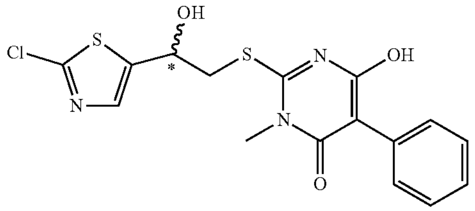

where the asterisk * shows the stereogenic center;

or of a tautomer thereof;

with an activating agent which enhances electrophilicity of the carbon atom marked with the asterisk in the compound of formula 1 without promoting racemization at said carbon atom;

to obtain an enantiomerically enriched form of the compound of formula (I).

2. The method according to claim 1, where the activating agent is selected from the group consisting of $P(OR^1)_2Cl$, $P(OR^1)Cl_2$, $P({=}O)(OR^1)_2Cl$, $P({=}O)(OR^1)Cl_2$, where each $R^1$ in the four aforementioned compounds is independently $C_1$-$C_4$-alkyl; $PCl_3$, $P({=}O)Cl_3$, polyphosphoric acid, $P_4O_{10}$, Mitsunobu-type reagents, triphenylphosphine in combination with a halogenating agent, $SO_3$ complexes with Lewis bases selected from amines, carboxamides, and heteroaromatic compounds containing 1, 2, or 3 basic nitrogen ring atoms; $S(O)Cl_2$, $CH_3S(O)_2Cl$, carbonyldiimidazole (CDI), Vilsmeier reagent, complexes of N,N-dimethylformamide and/or N,N-dimethylacetamide with a Lewis acid; and mixtures of two or more of the aforementioned activating agents.

3. The method according to claim 2, where the activating agent is selected from the group consisting of $P(OR^1)_2Cl$, $P(OR^1)Cl_2$, $P({=}O)(OR^1)_2Cl$, where each $R^1$ in the three aforementioned compounds is independently $C_1$-$C_4$-alkyl;

$PCl_3$, $P(O)Cl_3$, $SO_3$/dimethyl formamide complex, $SOCl_2$, $CH_3S(=O)_2Cl$, CDI, and Mitsunobu-type reagents.

4. The method according to claim 3, where the activating agent is selected from the group consisting of dimethyl chlorophosphite ($P(OCH_3)_2Cl$), diethyl chlorophosphite ($P(OCH_2CH_3)_2Cl$), methyl dichlorophosphite ($P(OCH_3)Cl_2$), ethyl dichlorophosphite ($P(OCH_2CH_3)Cl_2$), $PCl_3$, $P(O)Cl_3$, $SO_3$/dimethyl formamide complex, $CH_3S(=O)_2Cl$, and CDI.

5. The method according to claim 4, where the activating agent is selected from the group consisting of dimethyl chlorophosphite ($P(OCH_3)_2Cl$), diethyl chlorophosphite ($P(OCH_2CH_3)_2Cl$), and $PCl_3$.

6. The method according to claim 5, where the activating agent is selected from the group consisting of dimethyl chlorophosphite ($P(OCH_3)_2Cl$) and diethyl chlorophosphite ($P(OCH_2CH_3)_2Cl$).

7. The method according to claim 1, where the compound of the formula 1 and the activating agent are used in a molar ratio of from 10:1 to 1:10.

8. The method according to claim 7, where the compound of the formula 1 and the activating agent are used in a molar ratio of from 1:1 to 1:4.

9. The method according to claim 1, where the reaction is carried out at a temperature of from −80 to 120° C.

10. The method according to claim 1, where the reaction is carried out in the presence of a solvent, where the solvent is selected from the group consisting of polar aprotic solvents, mixtures of polar aprotic solvents and water, $C_1$-$C_4$-alkyl acetates, chlorinated alkanes, aromatic solvents, heterocyclic solvents, and mixtures thereof.

11. The method according to claim 10, where the solvent is selected from the group consisting of dimethylformamide, diethylformamide, dibutylformamide, dimethylacetamide, tetrahydrofuran, mixtures of tetrahydrofuran and water, 2-methyltetrahydrofuran, the dioxanes, dimethylsulfoxide, acetonitrile, N-methylpyrrolidone, N-(n-butyl)-pyrrolidone, N-(tert-butyl)-pyrrolidone, sulfolane, dimethylcarbonate, diethylcarbonate, propylene carbonate, γ-valerolactone, N,N,N',N'-tetrabutyl urea, 1,3-dimethyl-2-imidazolinone, ethyl acetate, isopropyl acetate, dichloromethane, trichloromethane, dichloroethane, benzene, toluene, trifluorotoluene, the xylenes, chlorobenzene, dichlorobenzene, 4-formylmorpholine, dihydrolevoglucosenone, and mixtures thereof.

12. The method according to claim 11, where the solvent is selected from the group consisting of dimethylformamide, diethylformamide, dibutylformamide, dimethylacetamide, tetrahydrofuran, mixtures of tetrahydrofuran and water, 2-methyltetrahydrofuran, 1,4-dioxane, acetonitrile, ethyl acetate, dichloromethane, toluene, chlorobenzene and mixtures thereof.

13. The method according to claim 1, where the reaction is carried out in the presence of a base selected from the group consisting of alkali metal hydroxides, amines of the formula $NR^1R^2R^3$, where $R^1$, $R^2$, and $R^3$, independently of each other, are selected from the group consisting of hydrogen, $C_1$-$C_6$-alkyl, $C_3$-$C_6$-cycloalkyl, $C_1$-$C_4$-alkoxy, and $C_1$-$C_4$-alkoxy-$C_1$-$C_4$-alkyl, where at least one of $R^1$, $R^2$, and $R^3$ is not hydrogen; diamines of the formula $NR^1R^2$-A-$NR^3R^4$, where $R^1$, $R^2$, $R^3$, and $R^4$, independently of each other, are selected from the group consisting of hydrogen, $C_1$-$C_6$-alkyl, $C_3$-$C_6$-cycloalkyl, $C_1$-$C_4$-alkoxy, and $C_1$-$C_4$-alkoxy-$C_1$-$C_4$-alkyl, and A is $(CH_2)_2$ or $(CH_2)_3$; and a 5- or 6-membered saturated heterocyclic ring containing one nitrogen atom as ring member and optionally one further heteroatom selected from N and O as ring member, where the ring optionally carry 1 to 6 $C_1$-$C_4$-alkyl groups and/or 1 or 2 OH groups.

14. The method according to claim 13, where the base is selected from the group consisting of LiOH, NaOH, KOH, diethylamine, triethylamine, tributylamine, diisopropylethylamine, dimethylisopropylamine, ethyl-tert-butylamine, isopropyl-tert-butylamine, (2-methoxyethyl)methylamine, N,N-dicyclohexylmethylamine, N-cyclohexyldimethylamine, N,N,N',N'-tetramethylethylenediamine, N,N,N',N'-tetramethylpropylene-1,3-diamine, piperdine, N-methylpiperidine, 2,2,6,6-tetramethylpiperidine, N-methyl-2,6,6-tetramethylpiperidine, N-methyl-4-hydroxy-2,2,6,6-tetramethylpiperidine, morpholine, and N-methylmorpholine, where the bases can be used in supported from.

15. The method according to claim 1, for preparing (3R)-3-(2-chlorothiazol-5-yl)-8-methyl-7-oxo-6-phenyl-2,3-dihydrothiazolo[3,2-a]pyrimidin-4-ium-5-olate of formula (I-R)

(I-R)

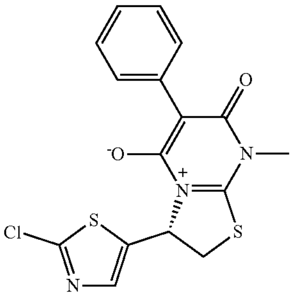

in an enantiomeric excess of at least 55% ee;

which method comprises reacting 2-[(2S)-2-(2-chlorothiazol-5-yl)-2-hydroxy-ethyl]sulfanyl-6-hydroxy-3-methyl-5-phenyl-pyrimidin-4-one of formula 1-S

1-S

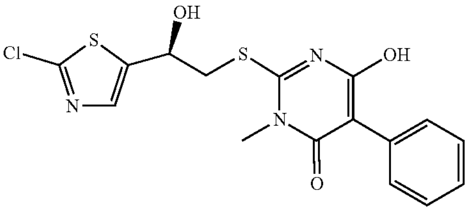

or a tautomer thereof with an activating agent.

16. The method according to claim 1, for preparing (3S)-3-(2-chlorothiazol-5-yl)-8-methyl-7-oxo-6-phenyl-2,3-dihydrothiazolo[3,2-a]pyrimidin-4-ium-5-olate of formula (I-S)

(I-S)
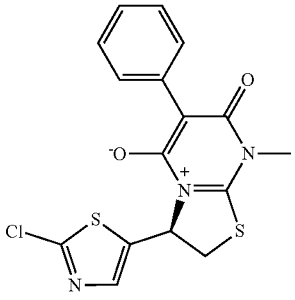
in an enantiomeric excess of at least 55% ee;
which method comprises reacting 2-[(2R)-2-(2-chlorothiazol-5-yl)-2-hydroxy-ethyl]sulfanyl-6-hydroxy-3-methyl-5-phenyl-pyrimidin-4-one of formula 1-R
1-R
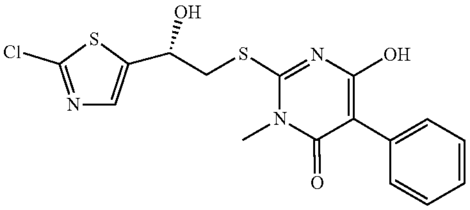
or a tautomer thereof with an activating agent.
* * * * *